(12) United States Patent
Tiwari (10) Patent No.: US 12,121,660 B2
(45) Date of Patent: Oct. 22, 2024

(54) OXYGEN FACE MASK WITH FILTER

(71) Applicant: Anil K Tiwari, Corona Del Mar, CA (US)

(72) Inventor: Anil K Tiwari, Corona Del Mar, CA (US)

(*) Notice: Subject to any disclaimer, the term of this patent is extended or adjusted under 35 U.S.C. 154(b) by 798 days.

(21) Appl. No.: 16/876,146

(22) Filed: May 18, 2020

(65) Prior Publication Data

US 2021/0353890 A1    Nov. 18, 2021

(51) Int. Cl.
*A61M 16/06* (2006.01)
*A61M 16/00* (2006.01)
(Continued)

(52) U.S. Cl.
CPC .... *A61M 16/0622* (2014.02); *A61M 16/0057* (2013.01); *A61M 16/0683* (2013.01);
(Continued)

(58) Field of Classification Search
CPC ........ A61M 16/047; A61M 2202/0208; A61M 16/0816; A61M 16/06; A61M 16/0057; A61M 16/0683; A61M 2016/103; A61M 2016/102; A61M 2016/1025; A61M 16/0875; A61M 16/0093; A61M 16/00; A61M 16/0003; A61M 16/0463; A61M 16/1005; A61M 2016/0661; A61M 2205/75; A61M 16/12; A61M 16/0622; A61M 16/041; A61M 16/0605; A61M 16/0611; A61M 16/0616; A61M 16/0627; A61M 16/0633; A61M 16/0638; A61M 16/0644; A61M 16/065; A61M 16/0655; A61M 16/0672; A61M 16/0677; A61M 16/0688; A61M 16/0694; A61M 2205/7509; A61M 2205/7518; A61M 2205/7527; A61M 2205/7536;
(Continued)

(56) References Cited

U.S. PATENT DOCUMENTS 2,104,016 A  *  1/1938  Biggs ................... A62B 18/025
                                              55/DIG. 35
3,782,083 A  *  1/1974  Rosenberg ............. B01D 46/10
                                              55/501
(Continued)

FOREIGN PATENT DOCUMENTS

WO    WO-2012103490 A1  *  8/2012  ............. A61B 5/082

*Primary Examiner* — Annette Dixon
(74) *Attorney, Agent, or Firm* — Cittone Demers & Arneri LLP; Henry J. Cittone (57) ABSTRACT

A clear, soft and malleable plastic constructed face mask is provided that has an elastic strap that is used to secure the mask onto a patient's face. The mask comprises of a malleable aluminium strip on the top for easy molding of the mask around the patient's nose; a front opening covered with a paper filter; and two side openings covered with a paper filter. The mask provides supplemental oxygen through connection to a Y-shaped respiratory/ventilator circuit or standard oxygen tubing. The mask also allows the patient to breathe comfortably without a supplemental oxygen source. It has ribbed tubing for gas sampling. The mask allows a health care employee to visualize breathing on the clear plastic material. The mask provides filtration of aerosolized contaminants.

16 Claims, 7 Drawing Sheets

(51) Int. Cl.
*A61M 16/08* (2006.01)
*A61M 16/10* (2006.01)

(52) U.S. Cl.
CPC ...... *A61M 16/0833* (2014.02); *A61M 16/085* (2014.02); *A61M 16/107* (2014.02); *A61M 2202/0208* (2013.01)

(58) Field of Classification Search
CPC .. A61M 2205/7545; A61M 2205/7554; A61M 2205/7563; A61M 2205/7572; A61M 2205/7581; A61M 2205/759; A61M 16/1055; A61M 16/0883; A61M 16/0891; A61M 16/10; A61M 16/0841–085; A61M 16/106–107; A61M 2202/0225; A61M 16/105–1095; A61M 16/08–0833; A61M 2230/432; A61M 11/00; A61M 11/006; A61M 11/02; A61M 11/06; A61M 15/00; A61M 15/0016; A61M 15/0018; A61M 15/0086; A61M 15/0088; A61M 15/009; A61M 15/08; A61M 15/085; A61M 16/0009; A61M 16/0045; A61M 16/0048; A61M 16/0051; A61M 16/0078; A61M 16/0087; A61M 16/009; A61M 16/01; A61M 16/024; A61M 16/04; A61M 16/0461; A61M 16/0488; A61M 16/049; A61M 16/0493; A61M 16/0666; A61M 16/0808; A61M 16/0825; A61M 16/0858; A61M 16/0866; A61M 16/101; A61M 16/1015; A61M 16/104; A61M 16/1045; A61M 16/1065; A61M 16/125; A61M 16/127; A61M 16/14; A61M 16/16; A61M 16/18; A61M 16/20; A61M 16/201; A61M 16/208; A61M 16/22; A61M 2016/0009; A61M 2016/0027; A61M 2016/0039; A61M 2202/0007; A61M 2202/0085; A61M 2202/0275; A61M 2202/0283; A61M 2202/062; A61M 2205/0205; A61M 2205/0227; A61M 2205/0238; A61M 2205/05; A61M 2205/18; A61M 2205/3327; A61M 2205/42; A61M 2205/502; A61M 2205/581; A61M 2205/582; A61M 2205/584; A61M 2205/6045; A61M 2205/6054; A61M 2205/6072; A61M 2205/70; A61M 2209/06; A61M 2210/005; A61M 2210/0612; A61M 2210/0618; A61M 2210/0625; A61M 2210/1053; A61M 2230/005; A61M 2230/202; A61M 2230/205; A61M 2230/42; A61M 2230/43; A61M 2230/435; A61M 2240/00; A61M 39/20; A41D 13/11; A41D 13/1281; A41D 13/1161; A41D 13/1138; A41D 13/1146; A41D 13/1176; A41D 13/1192; A62B 7/10; A62B 18/025; A62B 18/02; A62B 18/08; A62B 7/12; A62B 23/00; A62B 23/02; A62B 23/025; A62B 18/00; A62B 9/00; A62B 18/10; A62B 9/04; A62B 18/021; A62B 18/006; A62B 18/04; A62B 18/084; A62B 19/00; A62B 7/02; A62B 7/14; A62B 9/003; A62B 9/006; A62B 9/02; A63B 23/18; B64D 2231/025; A61J 1/1475; B01D 46/0012; B01D 2239/0241; B01D 2239/0622; B01D 2239/065; B01D 39/1623; B01D 39/1692; A61B 5/0836; A61B 1/00147; A61B 1/01; A61B 1/267; A61B 1/2676; A61B 1/2736; A61B 5/082; A61B 5/087; A61B 5/097; A61B 5/4821; A61B 5/6803; A61B 5/746; A61B 7/023; A61B 90/05; B29C 2791/001; B29C 51/00; B29K 2023/06; B29L 2031/4835; B29L 2031/753; B60H 1/00264; B60H 3/06; F16L 11/12; F16L 11/15; F16L 37/02; F16L 37/23; G01N 33/004; G01N 33/497; Y10S 128/909; Y10S 128/91; Y10S 128/912; Y10S 55/35; Y10T 137/2544; Y10T 137/87595; Y10T 137/87627; Y10T 29/49826

See application file for complete search history.

(56) References Cited

U.S. PATENT DOCUMENTS

| | | | | |
|---|---|---|---|---|
| 3,977,432 A * | 8/1976 | Vidal | .................. | A61M 16/127 137/893 |
| 4,231,359 A * | 11/1980 | Martin | .................. | A62B 17/04 128/206.29 |
| 4,440,163 A * | 4/1984 | Spergel | .................. | A62B 18/04 128/205.21 |
| 4,649,912 A * | 3/1987 | Collins | .................. | A62B 7/12 128/202.13 |
| 5,375,592 A * | 12/1994 | Kirk | .................. | A61M 16/0488 422/85 |
| 5,400,781 A * | 3/1995 | Davenport | .......... | A61M 16/085 128/206.28 |
| 5,474,060 A * | 12/1995 | Evans | .................... | A61B 5/097 128/204.22 |
| 6,659,102 B1 * | 12/2003 | Sico | .................... | A61M 16/06 128/206.28 |
| 8,960,195 B2 | 2/2015 | Lehman | | |
| 9,132,251 B2 * | 9/2015 | Johansen | .............. | A61M 16/06 |
| 10,335,569 B2 | 7/2019 | Beard et al. | | |
| 2002/0148464 A1 * | 10/2002 | Hoenig | ................. | A61M 16/08 128/200.24 |
| 2004/0069306 A1 * | 4/2004 | Moenning | ............ | A61M 16/06 128/206.18 |
| 2009/0235932 A1 * | 9/2009 | Nashed | ............ | A61M 16/0816 128/203.29 |
| 2011/0083670 A1 * | 4/2011 | Walacavage | ........ | A61M 16/107 128/205.12 |
| 2011/0108035 A1 * | 5/2011 | Samaniego | .......... | A62B 18/025 264/319 |
| 2012/0285468 A1 * | 11/2012 | Birch | ................ | A61M 16/0051 128/206.24 |
| 2016/0030695 A1 * | 2/2016 | Chang | .................. | A61M 16/06 128/205.25 |
| 2018/0110951 A2 | 4/2018 | Beard | | |
| 2021/0138174 A1 * | 5/2021 | Nelson | .............. | A61M 16/0833 |

* cited by examiner

FIG. 1

(Prior Art)

OXYGEN FACE MASK WITH FILTER

FIELD OF THE INVENTION

The present invention relates to a filter mask for reducing the risk of infection to the patient and facilitating oxygen delivery to the patient. More particularly, it relates to a mask configured to serve as both a filter surgical mask and oxygen mask for patients undergoing medical and surgical procedures.

BACKGROUND

A surgical mask, procedure mask or filter mask is intended to be worn by health professionals during surgery and certain health care procedures. The surgeons, nurses, and technicians wear these surgical masks to reduce the risk of infection while inside an operating room with sterile equipment and supplies. However, when patients enter the operating room, they are not wearing a surgical mask, which may increase the risk of infection. Due to the need to access the patient's airway and possibly provide supplemental oxygen, a surgical mask is usually not worn by the patient. According to a recent publication of the Association of periOperative Registered Nurses (AORN), "All individuals entering the restricted areas should wear a surgical mask when open sterile supplies and equipment are present".

In case of patients, delivery of supplemental oxygen might be needed in the operating room prior to induction of anesthesia or sedation. For example supplemental oxygen may be needed for patients who have cardiopulmonary disease, neurovascular disease or have previously received sedatives. So, to fulfil the aforementioned need, a surgical mask for a patient is required that has provision for providing oxygen to patient in operating room, when the need arises. It has been recognized that there is a need for a mask that can be used as both a surgical mask to a patient for reducing the risk of infection and has a provision for connecting to an oxygen supply source.

The existing solutions of the surgical mask have limitations in terms of providing protection against microorganisms, user comfort, and accurate sampling of breath. The presently available medical devices do not have a filter for the patient's breath, provide a built-in gas sampling tubing and a port for a respiratory circuit to provide supplemental oxygen.

The existing solution does not allow easy length adjustment/correction of the gas sampling tubing through the nose or mouth and it results in inaccuracies in measuring oxygen and carbon dioxide levels. Hence, there exists a need for a mask with expiratory gas sampling that provides protection against microorganisms, user comfort and can provide supplemental oxygen.

In order to overcome the above-mentioned problems, the present invention provides a simple moderate oxygen concentrator mask that allows patients to wear a filtered mask while inside an operating room so as to reduce the risk of infection while also providing supplemental oxygen delivery. The surgical oxygen mask includes a clear, soft and malleable plastic construction with an elastic strap that is used to secure it on a patient's face. The mask comprises of a malleable aluminium strip on the top to mold the mask around the patient's nose; a front opening covered with a paper filter; and two side openings covered with paper filters. The mask allows a connection to a respirator or ventilator circuit to provide supplemental oxygen and has ribbed tubing for gas sampling.

SUMMARY

This section provides a general summary of the disclosure and is not a comprehensive disclosure of its full scope or all of its features.

The present invention provides a filter surgical mask to prevent infection when they enter operating room and during surgery when a mask is required. The surgical oxygen mask includes a clear, soft and malleable plastic construction with an elastic strap that is used to secure it on a patient's face. The mask comprises of a malleable aluminium strip on the top to mold the mask around the patient's nose; a front opening covered with a paper filter; and two side openings covered with paper filters. The mask allows a connection to a ventilator circuit to provide supplemental oxygen and has ribbed tubing for gas sampling.

One aspect of the present invention provides a face mask for delivering breathable gas to a patient, the face mask comprising: a mask body defining a cavity configured to be positioned over the mouth and nose of a patient or user; at least one side filter allowing the patient to breath with minimal effort; a ribbed tubing configured to connect to a gas sampling tubing for sampling exhaled breath from a user or patient, the said ribbed tubing allows the gas sampling tubing to be adjusted to the correct length of sampling breathing through the nose or mouth; a inlet port for directing a flow of gas to the interior of the face mask, the inlet port having: a groove to allow the gas get into the mask; a filter to reduce the risk of microorganisms entering the operating room; a ring having two ends; wherein first end is configured to form a protruding ridge to attach the circular filter on the mask and the second end is configured to form an adapter facilitating to connect different standard connectors for gas supply.

Further areas of applicability will become apparent from the description provided herein.

BRIEF DESCRIPTION OF DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings.

DETAILED DESCRIPTION

In the following detailed description of embodiments of the invention, numerous specific details are set forth in order to provide a thorough understanding of the embodiment of invention. However, it will be obvious to a person skilled in art that the embodiments of invention may be practiced with or without these specific details. In other instances well known methods, procedures and components have not been described in detail, so as not to unnecessarily obscure aspects of the embodiments of the invention.

The terminology used herein is for the purpose of describing particular embodiments only and is not intended to be limiting of the invention. As used herein, the term "and/or" includes any and all combinations of one or more of the associated listed items. As used herein, the singular forms "a", "an", and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention discloses a concentrator oxygen mask that when worn by a patient undergoing a surgical procedure prevents him from contamination of the operating room. The present surgical oxygen mask is a clear, soft and malleable plastic construction and has an elastic strap that is used to secure the mask onto a patient's face. The mask comprises of a malleable aluminium strip on the top for easy molding of the mask around the patient's nose; a front opening covered with a paper filter; and two side openings covered with paper filters. The mask allows connection to a ventilator circuit for supplemental oxygen. It has ribbed tubing for gas sampling. The mask allows a health care employee to visualize breathing on the clear plastic material.

Figure 1:
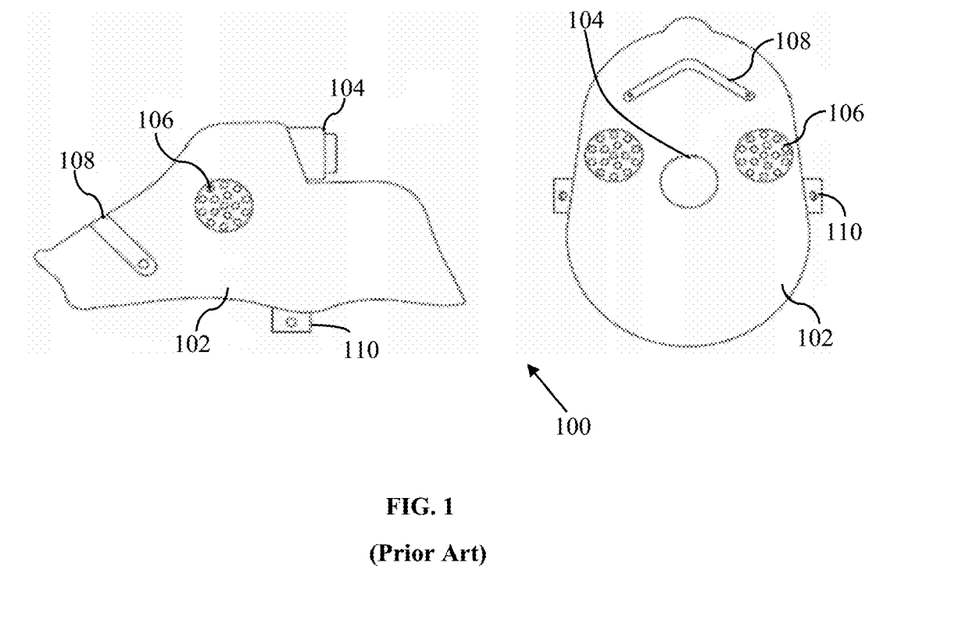
FIG. 1 shows a perspective view of conventionally available oxygen mask.

FIG. 1 shows a perspective view of conventionally available oxygen mask. Referring to FIG. 1, a conventional oxygen mask 100 comprises a mask body 102, an inlet port 104, vent ports 106, a nose clip 108 and strap attachments 110. The conventional oxygen mask 100 configured to supply the oxygen to the patient while undergoing medical procedures. The conventional oxygen mask does not provide an filtering ability, as it has perforated holes as vent ports 106, allowing microorganisms from the patient's breath to become aerosolized in the operating room. A conventional oxygen mask 100 cannot be worn unless connected to oxygen source, thus is not commonly worn during patient transport unless a portable oxygen source is available. A conventional oxygen mask 100 fails to serve as a surgical mask to protect against microorganism contamination of the operating room as specified by AORN. A conventional oxygen mask 100 does not allow connection to a ventilator circuit for supplemental oxygen. Moreover, the vent ports are generally formed near the nasal area of the conventional oxygen masks. For example, in the illustrated conventional oxygen mask, the vent ports 106 are formed on the upper half of the mask body 102. When the conventional oxygen mask 100 is worn, the unfiltered vent ports 106 are small and restrict ease of breathing without a supplemental oxygen source.

Figure 2:
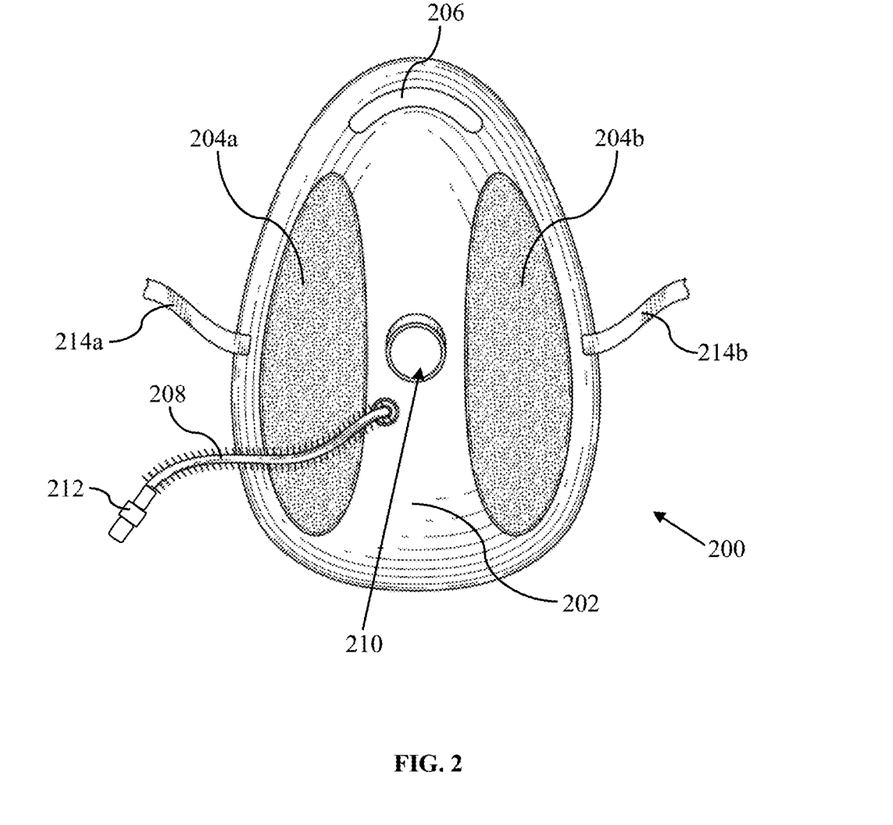
FIG. 2 shows a front view of face mask in accordance with an embodiment of the present invention.

FIG. 2 shows a front view of face mask in accordance with an embodiment of the present invention. Referring to FIG. 2, the face mask 200 comprises a mask body 202 defining a cavity configured to be positioned over the mouth and nose of a patient or user, an inlet port 210 for directing a flow of gas to the interior of the face mask 200, a malleable strip 206 to mold the mask around the patient's or user's nose, two side filters 204a and 204b allow the patient to breathe with minimal effort, strap attachments 214a and 214b to secure the mask body to the patient's or user's head, a ribbed tubing 208 designed to connect to a gas sampling tubing for sampling exhaled breath from a user or patient and a luer lock connector 212 attached to the end of ribbed tubing so as to connect the ribbed tubing with the gas sampling tubing.

The mask body 202 is generally molded of a gas-impermeable material, such as non-toxic medical grade plastic polymer material. The mask body 202 material can be transparent to allow clinicians or health care personnel to observe the patient's condition and condensation which indicates breathing on the clear plastic. The mask body 202 and connections and attachments thereto may be disposable. In another embodiment of the present invention the mask body 202 is made of silicone or polyvinyl chloride.

The mask body 202 defines a cavity adapted to fit over the mouth and the nose of the patient or the user. The peripheral edge of the mask body 202 is contoured so as to substantially seal against the surrounding facial tissue of the patient to establish an inner chamber portion or inner-space. The peripheral edge can be any shape as long as it is contoured so as to substantially seal against the surrounding facial tissue of the patient. The peripheral edge may be formed to include one or more recesses to allow nasal cannula to access the inner-space.

In an embodiment of the present invention the perimeter lining of mask 200 can be lined with non-permeable or semi-permeable material to inhibit an inner-space of the mask body from substantial contamination with room air when the oxygen mask is in use. The perimeter lining can be made of various materials including, but not limited to, cushion, padding, foam, and elastic. The perimeter lining may be formed integrally and unitarily with the mask body 202 or may be formed separately and permanently joined to the mask body. The perimeter lining may be thinner than the other areas of the mask body, for example, 20-40% thinner.

The face mask 200 comprises an inlet port 210 for directing a flow of gas to the interior of the face mask 200. In various embodiments, the inlet port 210 can be configured to accept any type of oxygen tube. The inlet port 210 allows oxygen to flow from an oxygen source to the inner-space of the face mask 200. The inlet port 210 is formed on the upper half of the mask body 202.

In another embodiment of the present invention the inlet port 210 is formed right above the half-way line that separates the upper half and the bottom half of the mask body 202. In this manner, the inlet port 210 is located around the nostrils of the patient when the face mask 200 is worn allowing oxygen to be delivered to the nasal area.

The filters 204a and 204b are disposed on both sides (i.e. left side and right side) of the mask body 202 to allow the patient to breathe with minimum effort. The face mask 200 of the present invention configured to serve as a surgical mask to a patient for reducing the risk of contaminating the sterility of an operating room and equipped with the mechanism to supply oxygen to the patient undergoing medical procedures. The filters 204a and 204b are composed of, but not limited to, paper, mats of nonwoven fibrous materials, such as wool felt, fiberglass paper, or polypropylene.

In the preferred embodiment of the present invention the filters 204a and 204b may comprise a housing containing a paper to filter out various undesirable materials (such as pathogens) in order to reduce the risk of infection to the patient. In case, the patient or user uses the face mask 200 as a surgical mask, the filters 204a and 204b filter out the contamination and various undesirable materials of the operating room and allow the patient to breathe with minimum effort. The filters 204a and 204b may each be any shape or size in order to optimize filtering while eliminating (or reducing) resistance to breathing.

In various embodiments, the filters 204a and 204b may be formed integrally with the molded mask body 202 or may be inserted into the mask body 202. The filters are attachable or connectable as accessories in various ways.

The face mask 200 comprises strap attachments 214a and 214b to secure the mask to the patient's or user's head. The face mask 200 may include any number of strap attachments. In the illustrated embodiment, the face mask 200 includes two strap attachments 214a and 214b. The two strap attachments 214a and 214b are disposed on opposing sides of the mask body 202 and are integrally molded with the mask body. In various embodiments, the strap attachments can be separate pieces from the mask body and attached to the mask body through different means (e.g., adhesive, fasteners, and screws). The strap attachments 214a and 214b may include holes disposed thereon to allow straps to be attached to the strap attachments 214a and 214b. Preferably, the two strap attachments 214a, 214b are configured to receive a conventional adjustable elastic retaining strap to secure the mask body to the patient's head.

The face mask 200 may comprise a malleable strip 206 to mold the mask around the patient's or user's nose. Preferably, the adjustable malleable strip 206 is disposed on the upper half of the mask body 202 such that the malleable strip 206 is over the nose when the face mask 200 is worn. The malleable strip 206 can be adjusted to conform to the nose to stabilize the face mask 200 in position on the patient's face. The strip 206 can be made of various flexible materials. In the present embodiment the malleable strip 206 is made of a malleable material, preferably, aluminum.

The face mask 200 comprises a ribbed tubing 208 designed to connect with a gas sampling tubing for sampling exhaled breath or an expiratory gas from a user or patient. A luer lock connector 212 is attached to the outside end of ribbed tubing to connect to a gas sampling tubing. The inside end of the ribbed tubing is attached to the inside of the mask body through flange. The ribbed tubing 208 is positioned at the front of the face mask 200 and above the right side filter 204a. Preferably, the ribbed tubing 208 is positioned between the inlet port 210 and right side filter 204a. A luer lock connector 212 allows the ribbed tubing 208 to connect with the gas sampling tubing or conduit (not shown in FIG. 2). In one embodiment, the outside end may be a female luer end configured to fit with a male luer connector. In another embodiment, the outside end may be a male luer end configured to fit with a female luer connector.

In another embodiment of the present invention the ribbed tubing 208 may be positioned in any lateral position relative to the nose and mouth. Any type of gas sampling tubing or conduit may be used. In one example, sampling conduit may be flexible polyurethane tubing. Gas sampling conduit may have a narrow diameter; the diameter may be smaller than a diameter of an oxygen conduit and the like.

In another embodiment of the present invention, the ribbed tubing 208 may be removed by the user or health care professional if gas sampling is not needed or available.

The gas sampling tubing may be coupled to a device or sensor for sampling and/or analyzing an expiratory gas or exhaled gas of the face mask 200. The gas may be sampled from the gas sampling tubing or a component present with the gas may be sampled. A sampled gas may contain other component(s) such a therapeutic nebulized or aerosolized component or agent. A gas may be expired gas. An expired gas may be mixed, in part, with delivered oxygen, or room air before sampling. In one example, a gas may not contain expired air (e.g., if the patient is not breathing). In one example, carbon dioxide is sampled (capnography). In another example, oxygen is sampled. In another example, end tidal partial pressure of the gas (e.g., carbon dioxide) may be measured (or otherwise determined or calculated).

Figure 3:
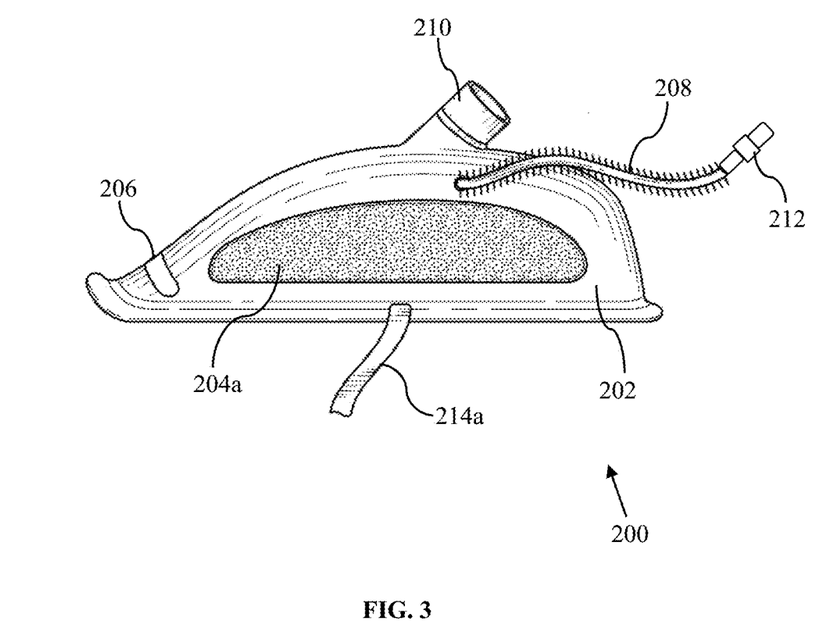
FIG. 3 shows a side view of the face mask in accordance with an embodiment of the present invention.

FIG. 3 shows a side view of the face mask in accordance with an embodiment of the present invention. Referring to FIG. 3, the face mask 200 comprises a mask body 202 defining a cavity configured to be positioned over the mouth and nose of a patient or user, an inlet port 210 for directing a flow of gas to the interior of the face mask 200, a malleable strip 206 to mold the mask around the patient's or user's nose, side filter 204a allow the patient to breathe with minimal effort, strap attachments 214a and 214b to secure the mask body to the patient's or user's head, a ribbed tubing 208 designed to connect to a gas sampling tubing for sampling exhaled breath from a user or patient and a luer lock connector 212 attached to the end of ribbed tubing so as to connect the ribbed tubing with the gas sampling tubing.

The inlet port 210 for directing a suitable gas, usually oxygen or a mixture thereof, to interior of face mask 200 via inlet tube. The inlet port 210 may be configured to accept any type of oxygen tube. The inlet port 210 allows oxygen to flow from an oxygen source to the inner-space of the face mask 200 in order to supply oxygen to the patient while undergoing medical procedure. The inlet port 210 may be formed on the upper half of the mask body 202, for example, on either side of the mask body 202. In this manner, the inlet port 210 is located to the side of the nostrils of the patient when the face mask 200 is worn allowing oxygen to be delivered to the nasal area.

In the preferred embodiment, the inlet port 210 comprises a groove, a paper filter to cover the opening of the groove, a hard plastic ring having two ends, the first end is configured to form a protruding ridge to attach the paper filter to the groove and the second end is configured to form an adapter facilitating to connect different connectors for gas (like oxygen, air or a mixture of both) supply. The second end of the hard plastic ring can be attached to ventilator tubing for supplemental oxygen or an aerated connector that connects to standard oxygen tubing for supplying oxygen to the patient.

Figure 4:
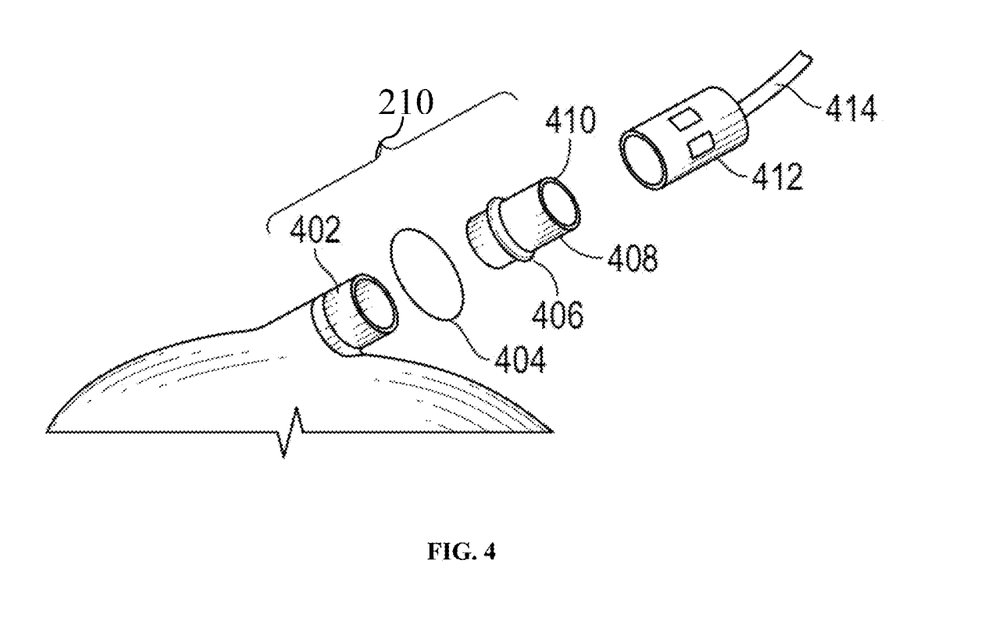
FIG. 4 illustrates the exemplary exploded view of the inlet port of the face mask in accordance with an embodiment of the present invention.

FIG. 4 illustrates the exemplary exploded view of the inlet port of the face mask in accordance with an embodiment of the present invention. Referring to FIG. 4, the inlet port 210 of the mask 200 comprises a groove 402 to allow the gas (like oxygen, air or a mixture of both) get into the mask, a filter 404 to prevent the patient's breath from contaminating the operating room, a ring 408 having two ends, the first end is configured to form a protruding ridge 406 to attach the filter 404 fitting with the groove 402 and the second end is configured to form an adapter 410 facilitating to connect different standard connectors for gas (like oxygen, air or a mixture of both) supply. The ring 408 can be made from one or a combination of materials, such as plastic, with sufficient strength and rigidity. In the preferred embodiment, the ring 408 is made of the hard plastic material. The second end of the ring 408 is configured to form an adapter 410 having the diameter including but not limited to, 14 mm, 15 mm, 16 mm, 17 mm, 18 mm, 19 mm, 20 mm, 21 mm, 22 mm and the like. Preferably, the diameter of the adapter 410 is 15 mm. The filter 404 which decreases contamination of the environment, the said filter 404 is composed of, but not limited to, paper, mats of nonwoven fibrous materials, such as wool felt, fiberglass paper, or polypropylene. In the preferred embodiment, the filter 404 is a paper filter.

In the preferred embodiment of the present invention the adapter 410 may be attached to a ventilator circuit for supplemental oxygen at varying concentrations of oxygen and/or air or mixture of both. The adapter 410 of the present invention connects to an aerated connector 412 that connects the oxygen tubing to face mask 200 for supplying oxygen to the patient. For example, in FIG. 4, an aerated connector 412 is shown having plurality of aeration holes and an oxygen tube 414 to supply the oxygen to the patient. The aerated connector 412 with aeration holes is having a diameter of 15 mm. The adapter 410 of the present invention is compatible to attach to a ventilator circuit for supplemental oxygen or an aerated connector 412 for supplying oxygen via tubing 414 to the patient. Therefore, no separate mask is required to connect the Y-piece of a ventilator circuit and standard oxygen tubing.

Figure 5:
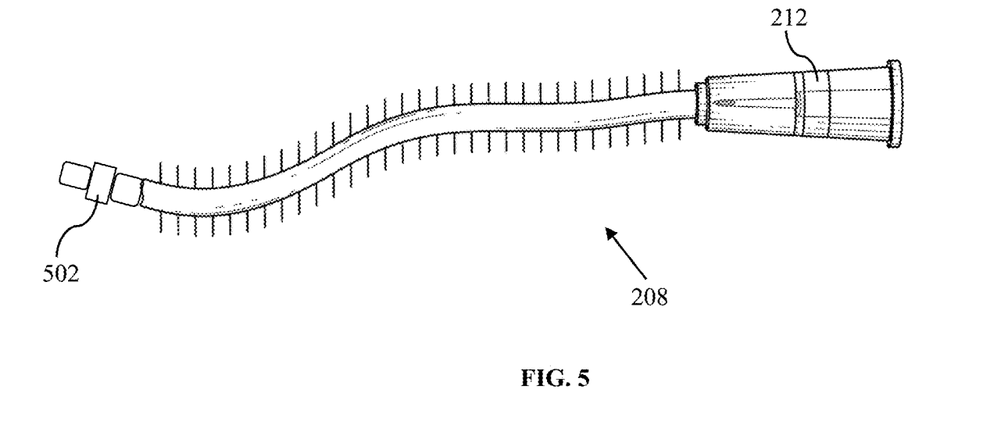
FIG. 5 illustrates the ribbed tubing in accordance with an embodiment of the present invention.

FIG. 5 illustrates the ribbed tubing in accordance with an embodiment of the present invention. Referring to FIG. 5, the ribbed tubing 208 designed to connect with a gas sampling tubing for sampling exhaled breath or an expiratory gas from a user or patient. A luer lock connector 212 is attached to first end of ribbed tubing so as to connect the ribbed tubing with the gas sampling tubing. The second end of the ribbed tubing is attached to the mask body through flange 502. The flange 502 pierce the plastic face mask and has a soft tip to prevent patient injury. The ribbed tubing 208 allows the sampling tubing to be adjusted to the correct length of sampling breathing through the nose or mouth. The length of the ribbed tubing including, but not limited to, 6 cm, 7 cm, 8 cm and the like. The ribbed tubing 208 is positioned at the front of the face mask 200 and above the right side filter 204a. Preferably, the ribbed tubing 208 is positioned between the inlet port 210 and right side filter 204a. A luer lock connector 212 allows the ribbed tubing 208 to connect with the gas sampling tubing or conduit (not shown in FIG. 5). In one embodiment, a first end may be a female luer end configured to fit with a male luer connector. In another embodiment, a first end may be a male luer end configured to fit with a female luer connector. A luer connector may be any size, but in some embodiments may have a maximum dimension (e.g., such as a maximum cross-sectional dimension in a longest dimension if the shape is not circular) of less than 5 mm, from 5 mm to 10 mm, from 10 mm to 15 mm, from 15 mm to 20 mm, from 20 mm to 30 mm, from 30 mm to 40 mm, or greater than 40 mm.

Figure 6:
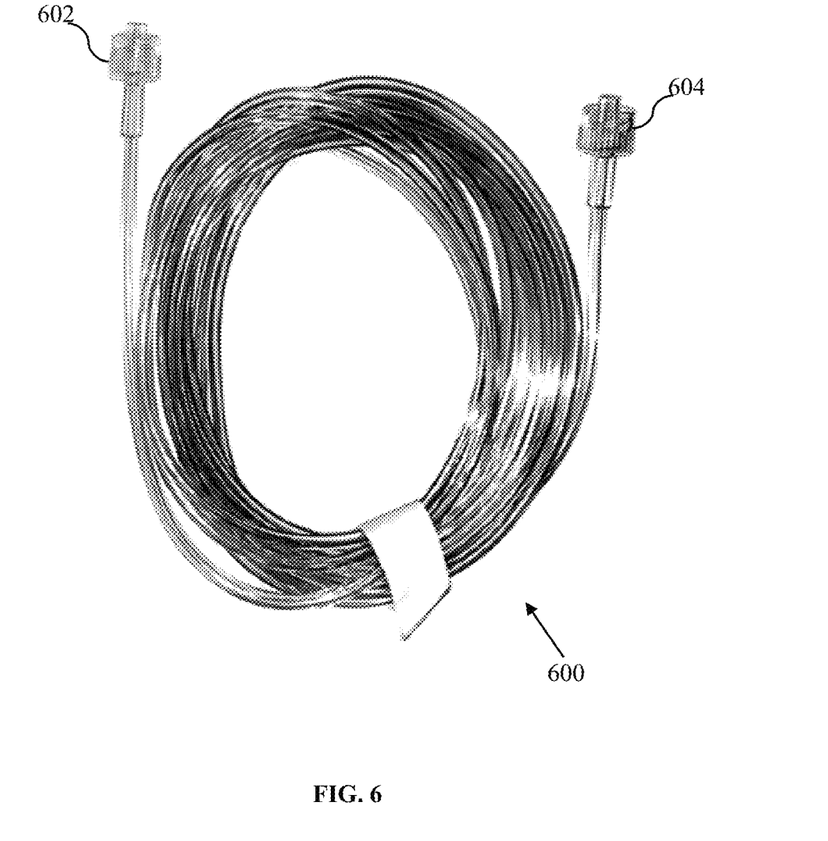
FIG. 6 illustrates the conventionally available gas sampling tubing that would attach to the ribbed tubing according to some embodiments of the present invention.

FIG. 6 illustrates the conventionally available gas sampling tubing that would attach to the ribbed tubing according to some embodiments of the present invention. Referring to FIG. 6, the gas sampling tubing 600 comprises two ends and both the ends include luer lock connectors. The one end 602 of the gas sampling tubing 600 may be connected to the face mask 200 through the ribbed tubing 208. The second end 604 of the gas sampling tubing 600 may be coupled to a device or sensor or a gas analysis machine for sampling and/or analyzing an expiratory gas or exhaled gas of the face mask 200. The face mask 200 comprises a ribbed tubing 208 designed to connect with a gas sampling tubing for sampling and/or analyzing exhaled breath or an expiratory gas from a user or patient. The luer lock connector 602 allows the gas sampling tubing or conduit 600 to connect with the ribbed tubing 208 (not shown in FIG. 6). The gas sampling tubing may be coupled to a device or sensor or gas analysis machine through luer lock connector 602 for sampling and/or analyzing an expiratory gas or exhaled gas of the face mask 200. The gas may be sampled from the gas sampling tubing or a component present with the gas may be sampled. A sampled gas may contain other component(s) such a therapeutic nebulized or aerosolized component or agent. A gas may be expired gas. An expired gas may be mixed, in part, with delivered oxygen, or room air before sampling. In one example, a gas may not contain expired air (e.g., if the patient is not breathing). In one example, carbon dioxide is sampled (capnography). In another example, oxygen is sampled. In another example, end tidal partial pressure of the gas (e.g., carbon dioxide) may be measured (or otherwise determined or calculated).

Preferably, the optimum samplings of exhaled air from the patient are maintained by having flange 502 provide a firm attachment of ribbed tubing with the mask body 202 of face mask 200 preventing air from the outside environment from transferring or leaking into interior of face mask 200 and contaminating the repeated samplings of the exhaled air stream by the patient.

In another embodiment of the present invention, the gas sampling tubing or conduit may be a flexible polyurethane tube. The gas sampling conduit may have a small diameter, which can be smaller than the diameter of the oxygen conduit. In one example, the sampling conduit may have an inner diameter of about ¼ inch or an outer diameter of ⅜ inch.

In another embodiment, the second end 604 of the gas sampling tubing 600 may be connected to a sensor. Any characteristic of the expiratory or exhaled gas can be sensed. Changes in gas volume, gas level, and/or gas pressure can be sensed. The partial pressure of the gas may be analyzed. In one example, carbon dioxide may be measured using an infrared sensor. In another case, carbon dioxide may be measured using a colorimetric sensor and the like.

Figure 7:
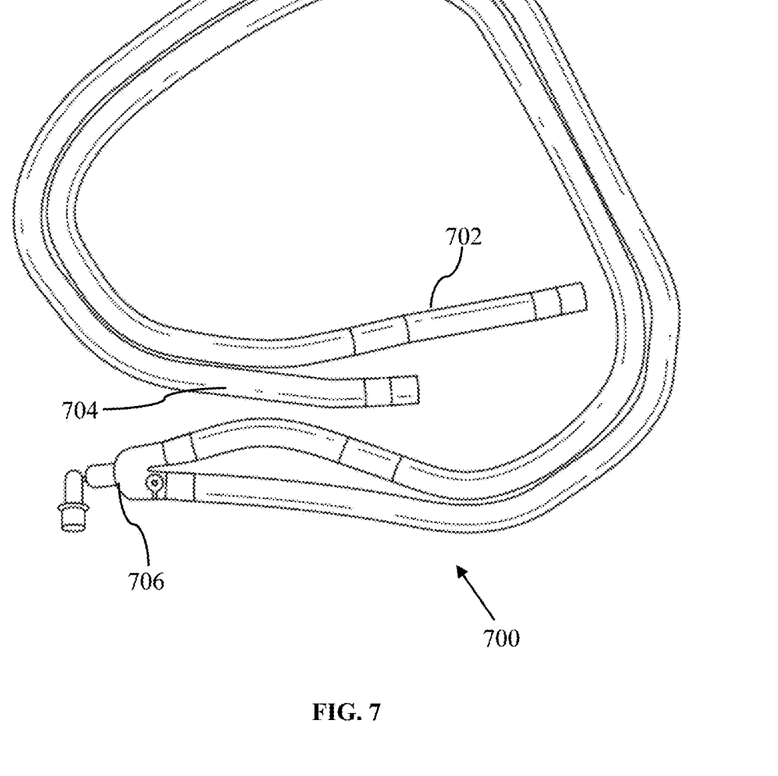
FIG. 7 illustrates a conventionally available ventilator circuit that would attach to the face mask according to some embodiments of the present invention.

FIG. 7 illustrates a conventionally available Y-piece 706 of a ventilator circuit/tubing that would attach to the face mask according to some embodiments of the present invention. The adapter 410 of the present invention is compatible to attach with Y-piece of a ventilator circuit 700 for supplemental oxygen supply. The adapter 410 of the inlet port 210 facilitates the face mask 200 compatible to attach with Y-piece of a ventilator circuit 700 for supplemental oxygen and an aerated connector for supplying oxygen to the patient. Referring to FIG. 7, the Y-piece of ventilator circuit/tubing 700 comprises two separate tubes 702 and 704 connected to a Y-shaped connector 706, hence its name coined as a Y-piece ventilator tubing. One of the tubes from 702 and 704 may flow the air to the patient after passing through a humidifier, which warms and moistens the air. The other tube carries the exhaled air away from the patient. The Y-piece of ventilator tubing is simple, lightweight, biologically inert, gas impermeable and allows low resistance and low compliance. The face mask 200 of the present invention is configured to be used with a ventilator or anesthesia machine to provide supplemental oxygen.

For additional details relating to the present invention, materials and manufacturing techniques of the level of ordinary skill in the art can be used. The same may be true for aspects based on the method of the present invention with respect to additional actions commonly or logically used.

Also, optional features of the described variations of the invention can be described and claimed independently or in combination with any one or more of the features described herein. Similarly, a reference to a singular element includes the possibility that there are pluralities of the same element. More specifically, the singular form ("a," "and," "said," and "the") is not expressly required by the context as used herein and in the appended claims. As long as it includes a plurality of instructions. It is further noted that the claims may be drafted to exclude optional elements.

Therefore, this statement should serve as a preceding basis for the use of exclusive terms such as "simply", "only", etc. or "negative" limitation in connection with the description of the elements of the claims is intended. Unless defined otherwise herein, all technical and scientific terms used herein have the same meaning as commonly understood by one of ordinary skill in the art to which this invention belongs. The scope of the invention is not limited by this specification, but only by the plain meaning of the terms used in the claims.

The invention claimed is:

1. A face mask for delivering breathable gas to a patient or a user, the face mask comprising:
    a mask body defining a cavity configured to be positioned over a mouth and nose of a patient or a user;
    at least one side filter permitting the patient to breathe;
    a ribbed tubing configured to connect to a gas sampling tubing for sampling exhaled breath of the patient or the user, said ribbed tubing can be stretched or compressed to decrease or increase a length of the gas sampling tubing;
    an inlet port for directing a flow of a gas to an interior of the face mask, the inlet port having:
        a groove to allow the gas get into the face mask;
        a filter to filter out various undesirable materials from the gas;
        a ring having a first end and a second end; wherein the first end is configured to form a protruding ridge to fit the filter over the groove and the second end is configured to form an adapter facilitating to connect different standard connectors for gas supply.

2. The face mask of claim 1, further comprising a malleable strip to mold the face mask around a nose of the patient or the user.

3. The face mask of claim 1, further comprising strap attachments to secure the mask body to a head of the patient or the user.

4. The face mask of claim 1, wherein the mask body is molded of a gas-impermeable material.

5. The face mask of claim 1, wherein the mask body having a peripheral edge in a contoured shape so as to substantially seal against the mouth of the patient or the user.

6. The face mask of claim 1, wherein the face mask comprises two side filters, a first filter at left side of the face mask and a second filter at right side of the face mask, to allow the patient or the user to breath without a connection to an oxygen tubing.

7. The face mask of claim 6, wherein the first filter and the second filter are composed of paper.

8. The face mask of claim 1, wherein a first end of the ribbed tubing having a luer lock connector so as to connect the ribbed tubing with the gas sampling tubing.

9. The face mask of claim 1, wherein a second end of ribbed tubing is attached to the mask body through a flange.

10. The face mask of claim 1, wherein the inlet port is formed on outer face of the mask body.

11. The face mask of claim 1, wherein the ring is made of a plastic material.

12. The face mask of claim 1, wherein the filter is attached with a groove to filter out various undesirable contaminants from entering or exiting the mask.

13. The face mask of claim 12, wherein the filter is composed of paper.

14. The face mask of claim 1, wherein the second end of the ring is an adapter of 15 mm diameter.

15. The face mask of claim 1, wherein the adapter is configured to attach to a ventilator circuit/tubing for supplemental oxygen.

16. The face mask of claim 1, wherein the adapter is configured to connect with standard aerated connector that connects an oxygen tubing to face mask for supplying oxygen to the patient.

* * * * *